US010991091B2

(12) United States Patent
Ezhov et al.

(10) Patent No.: US 10,991,091 B2
(45) Date of Patent: Apr. 27, 2021

(54) SYSTEM AND METHOD FOR AN AUTOMATED PARSING PIPELINE FOR ANATOMICAL LOCALIZATION AND CONDITION CLASSIFICATION (71) Applicant: Diagnocat, Inc., Wilimington, DE (US)

(72) Inventors: Matvey Dmitrievich Ezhov, Moscow (RU); Vladimir Leonidovich Aleksandrovskiy, Moscow (RU); Evgeny Sergeevich Shumilov, Moscow (RU)

(73) Assignee: Diagnocat Inc., Wilmington, DE (US)

( * ) Notice: Subject to any disclaimer, the term of this patent is extended or adjusted under 35 U.S.C. 154(b) by 115 days.

(21) Appl. No.: 16/175,067

(22) Filed: Oct. 30, 2018

(65) Prior Publication Data

US 2020/0134815 A1 Apr. 30, 2020

(51) Int. Cl.
*G06K 9/00* (2006.01)
*G06T 7/00* (2017.01)
*G06T 1/20* (2006.01)
*G06T 3/40* (2006.01)
*G06N 3/08* (2006.01)

(52) U.S. Cl.
CPC .......... *G06T 7/0012* (2013.01); *G06K 9/0057* (2013.01); *G06K 9/00503* (2013.01); *G06K 9/00536* (2013.01); *G06N 3/08* (2013.01); *G06T 1/20* (2013.01); *G06T 3/4007* (2013.01); *G06T 2207/30036* (2013.01)

(58) Field of Classification Search
CPC ....... G06T 7/0012; G06T 1/20; G06T 3/4007; G06T 2207/30036; G06K 9/0057; G06K 9/00536; G06K 9/00503; G06N 3/08; G16H 30/40; G16H 50/20
USPC ........................................................ 382/224
See application file for complete search history.

(56) References Cited

U.S. PATENT DOCUMENTS

| | | | |
|---|---|---|---|
| 6,102,704 A * | 8/2000 | Eibofner | A61B 5/7475 433/215 |
| 7,596,253 B2 * | 9/2009 | Wong | A61B 5/0088 382/128 |
| 7,664,298 B2 | 2/2010 | Lang | |
| 8,849,016 B2 | 9/2014 | Chen et al. | |
| 9,672,302 B2 | 6/2017 | Dean et al. | |
| 9,937,020 B2 | 4/2018 | Choi | |
| 10,204,414 B2 | 2/2019 | Andreiko et al. | |

(Continued)

*Primary Examiner* — Van D Huynh
(74) *Attorney, Agent, or Firm* — Patent Ventures, LLC (57) ABSTRACT An automated parsing pipeline system and method for anatomical localization and condition classification is disclosed. The system comprises an input even source, a memory unit and processor including a volumetric image processor, a voxel parsing engine, localization layer and a detection module. The volumetric image processor is configured to receive volumetric image from the input source and parse the received volumetric image. The voxel parsing engine is configured to assign each voxel a distant anatomical structure. The localization layer is configured to crop a defined anatomical structure with surroundings. The detection module is configured to classify conditions for each defined anatomical structure within the cropped image. The disclosed system and method provide accurate localization of a tooth and detects several common conditions in each tooth.

18 Claims, 10 Drawing Sheets

(56) References Cited

U.S. PATENT DOCUMENTS

| | | | |
|---|---|---|---|
| 2005/0058259 A1* | 3/2005 | Vija | A61B 6/583 |
| | | | 378/210 |
| 2006/0223032 A1* | 10/2006 | Fried | A61B 5/0088 |
| | | | 433/215 |
| 2008/0232539 A1 | 9/2008 | Pasini | |
| 2009/0274998 A1* | 11/2009 | Wong | A61B 5/0088 |
| | | | 433/215 |
| 2010/0121658 A1* | 5/2010 | Kaminski | G16H 50/20 |
| | | | 705/3 |
| 2012/0189182 A1* | 7/2012 | Liang | G16H 10/60 |
| | | | 382/131 |
| 2015/0320320 A1* | 11/2015 | Kopelman | G06T 7/344 |
| | | | 433/24 |
| 2015/0347682 A1 | 12/2015 | Chen et al. | |
| 2015/0359614 A1 | 12/2015 | Sachdeva | |
| 2016/0058408 A1* | 3/2016 | Kim | G06T 7/11 |
| | | | 382/131 |
| 2016/0117797 A1* | 4/2016 | Li | G06K 9/6211 |
| | | | 382/128 |
| 2018/0168781 A1* | 6/2018 | Kopelman | G16H 30/40 |
| 2018/0357766 A1* | 12/2018 | Van Der Poel | G06T 7/12 |
| 2019/0090993 A1* | 3/2019 | Engelmohr | G06T 7/0016 |
| 2019/0122411 A1* | 4/2019 | Sachs | G06T 19/20 |
| 2019/0180143 A1* | 6/2019 | Lyu | G06K 9/6271 |
| 2019/0320934 A1* | 10/2019 | Odry | G16H 40/20 |
| 2020/0100724 A1* | 4/2020 | Golay | G06F 21/6245 |
| 2020/0146646 A1* | 5/2020 | Tuzoff | G06T 7/0012 |

\* cited by examiner

SYSTEM AND METHOD FOR AN AUTOMATED PARSING PIPELINE FOR ANATOMICAL LOCALIZATION AND CONDITION CLASSIFICATION

BACKGROUND

Field

This invention relates generally to medical diagnostics, and more specifically to an automated parsing pipeline system and method for anatomical localization and condition classification.

Related Art

Modern image generation systems play an important role in disease detection and treatment planning. Few existing systems and methods were discussed as follows. One common method utilized is dental radiography, which provides dental radiographic images that enable the dental professional to identify many conditions that may otherwise go undetected and to see conditions that cannot be identified clinically. Another technology is cone beam computed tomography (CBCT) that allows to view structures in the oral-maxillofacial complex in three dimensions. Hence, cone beam computed tomography technology is most desired over the dental radiography.

However, CBCT includes one or more limitations, such as time consumption and complexity for personnel to become fully acquainted with the imaging software and correctly using digital imaging and communications in medicine (DICOM) data. American Dental Association (ADA) also suggests that the CBCT image should be evaluated by a dentist with appropriate training and education in CBCT interpretation. Further, many dental professionals who incorporate this technology into their practices have not had the training required to interpret data on anatomic areas beyond the maxilla and the mandible. To address the foregoing issues, deep learning has been applied to various medical imaging problems to interpret the generated images, but its use remains limited within the field of dental radiography. Further, most applications only work with 2D X-ray images.

Another existing article entitled "Teeth and jaw 3D reconstruction in stomatology", Proceedings of the International Conference on Medical Information Visualisation—BioMedical Visualisation, pp 23-28, 2007, researchers Krsek et al. describe a method dealing with problems of 3D tissue reconstruction in stomatology. In this process, 3D geometry models of teeth and jaw bones were created based on input (computed tomography) CT image data. The input discrete CT data were segmented by a nearly automatic procedure, with manual correction and verification. Creation of segmented tissue 3D geometry models was based on vectorization of input discrete data extended by smoothing and decimation. The actual segmentation operation was primarily based on selecting a threshold of Hounsfield Unit values. However, this method fails to be sufficiently robust for practical use.

Another existing patent number U.S. Pat. No. 8,849,016, entitled "Panoramic image generation from CBCT dental images" to Shoupu Chen et al. discloses a method for forming a panoramic image from a computed tomography image volume, acquires image data elements for one or more computed tomographic volume images of a subject, identifies a subset of the acquired computed tomographic images that contain one or more features of interest and defines, from the subset of the acquired computed tomographic images, a sub-volume having a curved shape that includes one or more of the contained features of interest. The curved shape is unfolded by defining a set of unfold lines wherein each unfold line extends at least between two curved surfaces of the curved shape sub-volume and re-aligning the image data elements within the curved shape sub-volume according to a re-alignment of the unfold lines. One or more views of the unfolded sub-volume are displayed.

Another existing patent application number US20080232539, entitled "Method for the reconstruction of a panoramic image of an object, and a computed tomography scanner implementing said method" to Alessandro Pasini et al. discloses a method for the reconstruction of a panoramic image of the dental arches of a patient, a computer program product, and a computed tomography scanner implementing said method. The method involves acquiring volumetric tomographic data of the object; extracting, from the volumetric tomographic data, tomographic data corresponding to at least three sections of the object identified by respective mutually parallel planes; determining, on each section extracted, a respective trajectory that a profile of the object follows in an area corresponding to said section; determining a first surface transverse to said planes such as to comprise the trajectories, and generating the panoramic image on the basis of a part of the volumetric tomographic data identified as a function of said surface. However, the above references also fail to address the afore discussed problems regarding the cone beam computed tomography technology and image generation system.

Therefore, there is a need for an automated parsing pipeline system and method for anatomical localization and condition classification.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. Embodiments disclosed include an automated parsing pipeline system and method for anatomical localization and condition classification.

In an embodiment, the system comprises an input event source, a memory unit in communication with the input event source, a processor in communication with the memory unit, a volumetric image processor in communication with the processor, a voxel parsing engine in communication with the volumetric image processor and a localizing layer in communication with the voxel parsing engine. In one embodiment, the memory unit is a non-transitory storage element storing encoded information. In one embodiment, at least one volumetric image data is received from the input event source by the volumetric image processor. In one embodiment, the input event source is a radio-image gathering source.

The processor is configured to parse the at least one received volumetric image data into at least a single image frame field of view by the volumetric image processor. The processor is further configured to localize anatomical structures residing in the at least single field of view by assigning each voxel a distinct anatomical structure by the voxel parsing engine. In one embodiment, the single image frame field of view is pre-processed for localization, which involves rescaling using linear interpolation. The pre-processing involves use of any one of a normalization schemes to account for variations in image value intensity depending on at least one of an input or output of volumetric image. In one embodiment, localization is achieved using a V-Net-based fully convolutional neural network.

The processor is further configured to select all voxels belonging to the localized anatomical structure by finding a minimal bounding rectangle around the voxels and the surrounding region for cropping as a defined anatomical structure by the localization layer. The bounding rectangle extends by at least 15 mm vertically and 8 mm horizontally (equally in all directions) to capture the tooth and surrounding context. In one embodiment, the automated parsing pipeline system further comprises a detection module. The processor is configured to detect or classify the conditions for each defined anatomical structure within the cropped image by a detection module or classification layer. In one embodiment, the classification is achieved using a DenseNet 3-D convolutional neural network.

In another embodiment, an automated parsing pipeline method for anatomical localization and condition classification is disclosed. At one step, at least one volumetric image data is received from an input event source by a volumetric image processor. At another step, the received volumetric image data is parsed into at least a single image frame field of view by the volumetric image processor. At another step, the single image frame field of view is pre-processed by controlling image intensity value by the volumetric image processor. At another step, the anatomical structure residing in the single pre-processed field of view is localized by assigning each voxel a distinct anatomical structure ID by the voxel parsing engine. At another step, all voxels belonging to the localized anatomical structure is selected by finding a minimal bounding rectangle around the voxels and the surrounding region for cropping as a defined anatomical structure by the localization layer. In another embodiment, the method includes a step of, classifying the conditions for each defined anatomical structure within the cropped image by the classification layer.

Other embodiments of this aspect include corresponding computer systems, apparatus, and computer programs recorded on one or more computer storage devices, each configured to perform the actions of the methods.

DETAILED DESCRIPTION

Specific embodiments of the invention will now be described in detail with reference to the accompanying FIGS. 1A-7. In the following detailed description of embodiments of the invention, numerous specific details are set forth in order to provide a more thorough understanding of the invention. In other instances, well-known features have not been described in detail to avoid obscuring the invention. Embodiments disclosed include an automated parsing pipeline system and method for anatomical localization and condition classification.

Figure 1A:
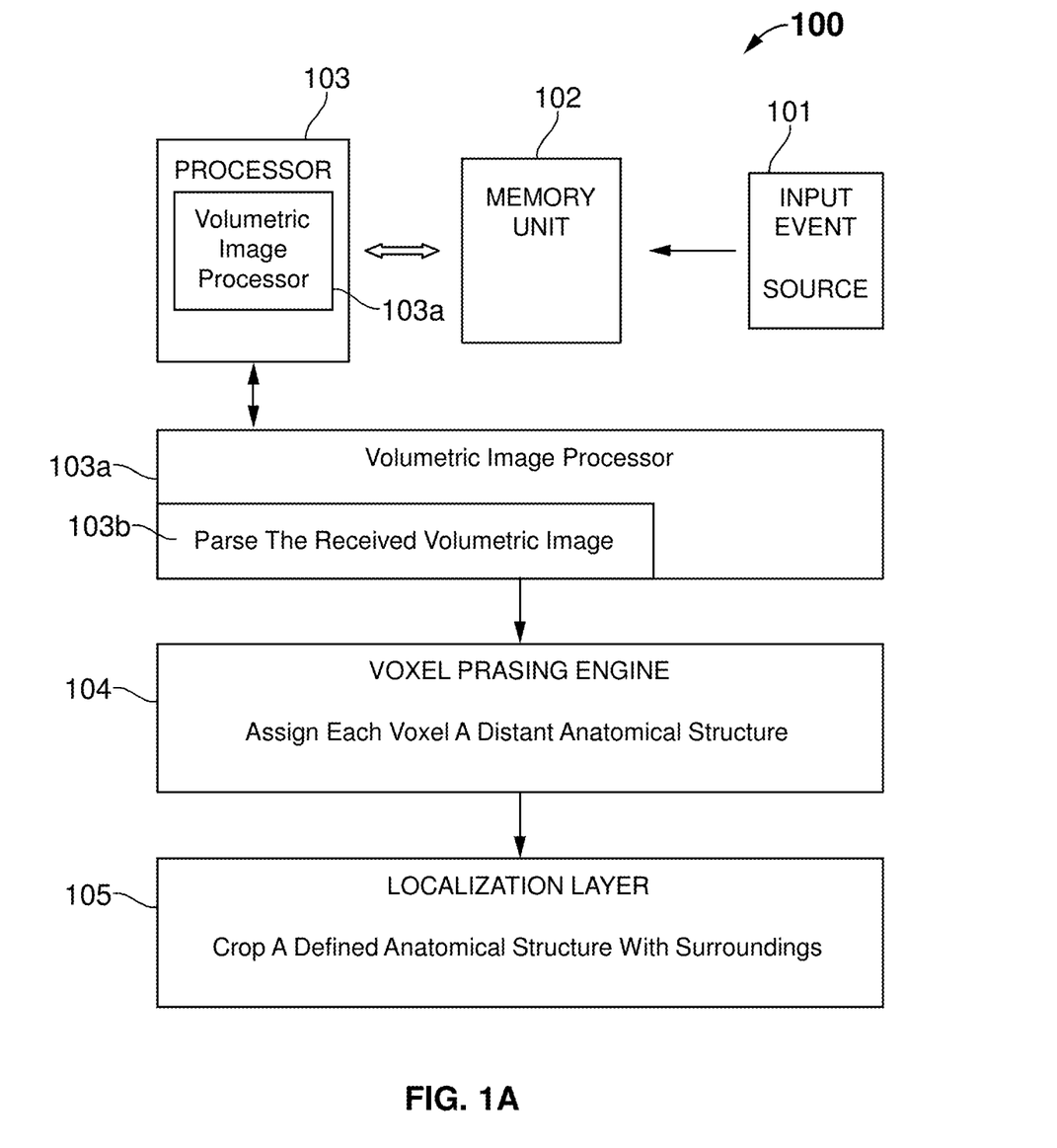
FIG. 1A illustrates in a block diagram, an automated parsing pipeline system for anatomical localization and condition classification, according to an embodiment.

FIG. 1A illustrates a block diagram 100 of the system comprising an input event source 101, a memory unit 102 in communication with the input event source 101, a processor 103 in communication with the memory unit 102, a volumetric image processor 103a in communication with the processor 103, a voxel parsing engine 104 in communication with the volumetric image processor 103a and a localizing layer 105 in communication with the voxel parsing engine 104. In an embodiment, the memory unit 102 is a non-transitory storage element storing encoded information. The encoded instructions when implemented by the processor 103, configure the automated pipeline system to localize an anatomical structure and classify the condition of the localized anatomical structure.

In one embodiment, an input data is provided via the input event source 101. In one embodiment, the input data is a volumetric image data and the input event source 101 is a radio-image gathering source. In one embodiment, the input data is 2D image data. The volumetric image data comprises 3-D pixel array. The volumetric image processor 103a is configured to receive the volumetric image data from the radio-image gathering source. Initially, the volumetric image data is pre-processed, which involves conversion of 3-D pixel army into an array of Hounsfield Unit (HU) radio intensity measurements.

The processor 103 is further configured to parse at least one received volumetric image data 103b into at least a single image frame field of view by the volumetric image processor.

The processor 103 is further configured to localize anatomical structures residing in the single image frame field of view by assigning each voxel a distinct anatomical structure by the voxel parsing engine 104. In one embodiment, the single image frame field of view is pre-processed for localization, which involves rescaling using linear interpolation. The pre-processing involves use of any one of a normalization schemes to account for variations in image value intensity depending on at least one of an input or output of volumetric image. In one embodiment, localization is achieved using a V-Net-based fully convolutional neural network. In one embodiment, the V-Net is a 3D generalization of UNet.

The processor 103 is further configured to select all voxels belonging to the localized anatomical structure by finding a minimal bounding rectangle around the voxels and the surrounding region for cropping as a defined anatomical structure by the localization layer. The bounding rectangle extends by at least 15 mm vertically and 8 mm horizontally (equally in all directions) to capture the tooth and surrounding context.

Figure 1B:
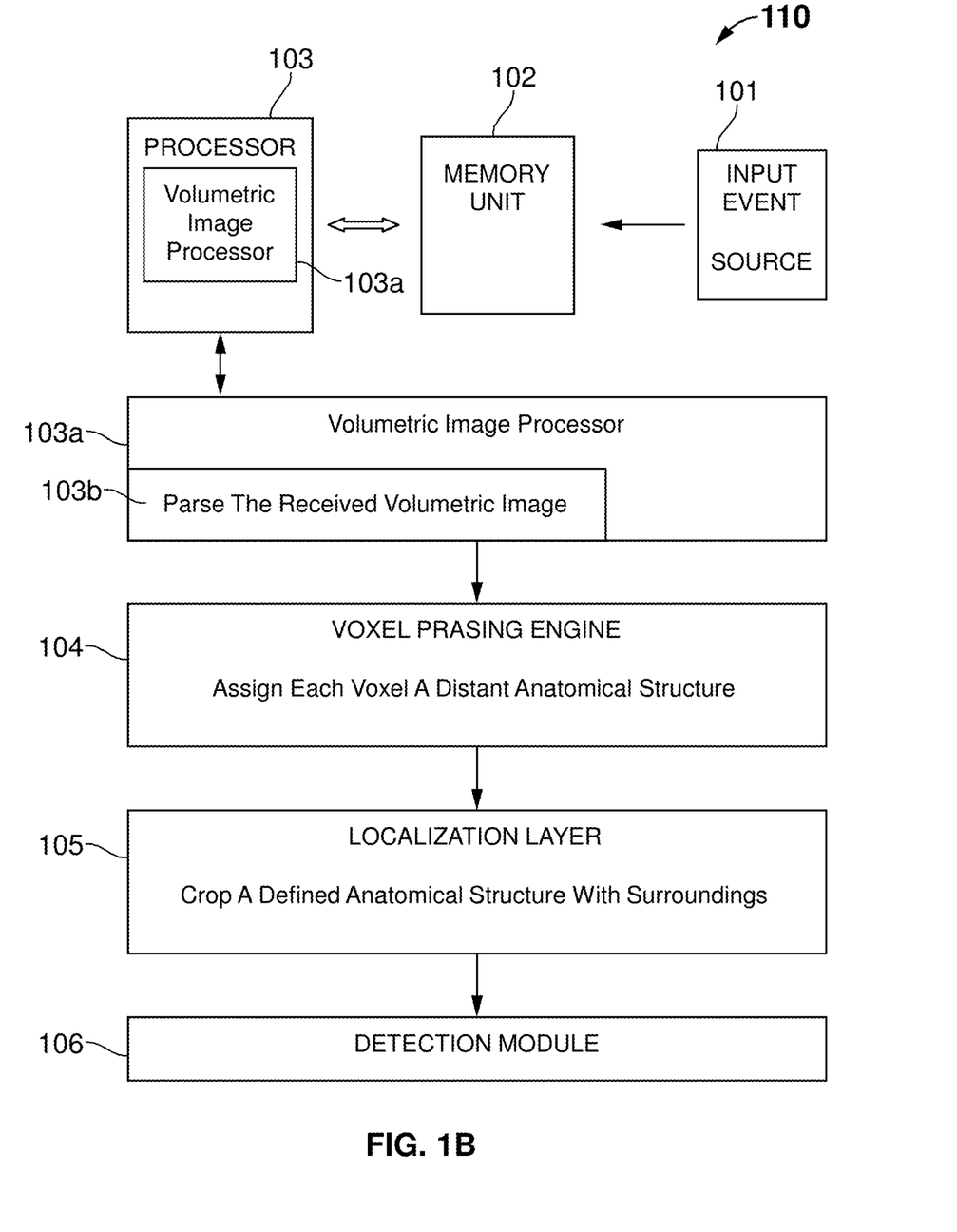
FIG. 1B illustrates in a block diagram, an automated parsing pipeline system for anatomical localization and condition classification, according to another embodiment.

FIG. 1B illustrates in a block diagram 110, an automated parsing pipeline system for anatomical localization and condition classification, according to another embodiment. The automated parsing pipeline system further comprises a detection module 106. The processor 103 is configured to detect or classify the conditions for each defined anatomical structure within the cropped image by a detection module or classification layer 106. In one embodiment, the classification is achieved using a DenseNet 3-D convolutional neural network.

In one embodiment, the localization layer 105 includes 33 class semantic segmentation in 3D. In one embodiment, the system is configured to classify each voxel as one of 32 teeth or background and resulting segmentation assigns each voxel to one of 33 classes. In another embodiment, the system is configured to classify each voxel as either tooth or other anatomical structure of interest. In case of localizing only teeth, the classification includes, but not limited to, 2 classes. Then individual instances of every class (teeth) could be split, e.g. by separately predicting a boundary between them. In some embodiments, the anatomical structure being localized, includes, but not limited to, teeth, upper and lower jaw bone, sinuses, lower jaw canal and joint.

In one embodiment, the system utilizes fully-convolutional network. In another embodiment, the system works on downscaled images (typically from 0.1-0.2 mm voxel resolution to 1.0 mm resolution) and grayscale (1-channel) image (say, 1×100×100×100-dimensional tensor). In yet another embodiment, the system outputs 33-channel image (say, 33×100×100×100-dimensional tensor) that is interpreted as a probability distribution for non-tooth vs. each of 32 possible (for adult human) teeth, for every pixel.

In an alternative embodiment, the system provides 2-class segmentation, which includes labelling or classification, if the localization comprises tooth or not. The system additionally outputs assignment of each tooth voxel to a separate "tooth instance".

In one embodiment, the system comprises VNet predicting multiple "energy levels", which are later used to find boundaries. In another embodiment, a recurrent neural network could be used for step by step prediction of tooth, and keep track of the teeth that were outputted a step before. In yet another embodiment, Mask-RCNN generalized to 3D could be used by the system. In yet another embodiment, the system could take multiple crops from 3D image in original resolution, perform instance segmentation, and then join crops to form mask for all original image. In another embodiment, the system could apply either segmentation or object detection in 2D, to segment axial slices. This would allow to process images in original resolution (albeit in 2D instead of 3D) and then inter 3D shape from 2D segmentation.

In one embodiment, the system could be implemented utilizing descriptor learning in the multitask learning framework i.e., a single network learning to output predictions for multiple dental conditions. This could be achieved by balancing loss between tasks to make sure every class of every task have approximately same impact on the learning. The loss is balanced by maintaining a running average gradient that network receives from every class*task and normalizing it. Alternatively, descriptor learning could be achieved by teaching network on batches consisting data about a single condition (task) and sample examples into these batches in such a way that all classes will have same number of examples in batch (which is generally not possible in multitask setup). Further, standard data augmentation could be applied to 3D tooth images to perform scale, crop, rotation, vertical flips. Then, combining all augmentations and final image resize to target dimensions in a single affine transform and apply all at once.

Advantageously, in some embodiment, to accumulate positive cases faster, weak model could be trained and run the model on all of unlabeled data. From resulting predictions, teeth model that gives high scores on some rare pathology of interest are selected. Then, the teeth are sent to be labelled by humans or users and added to the dataset (both positive and negative human labels). This allows to quickly and cost-efficiently build up more balanced dataset for rare pathologies.

In some embodiments, the system could use coarse segmentation mask from localizer as an input instead of tooth image. In some embodiments, the descriptor could be trained to output fine segmentation mask from some of the intermediate layers. In some embodiments, the descriptor could be trained to predict tooth number.

As an alternative to multitask learning approach, "one network per condition" could be employed, i.e. models for different conditions are completely separate models that share no parameters. Another alternative is to have a small shared base network and use separate subnetworks connected to this base network, responsible for specific conditions/diagnoses.

Figure 2A:
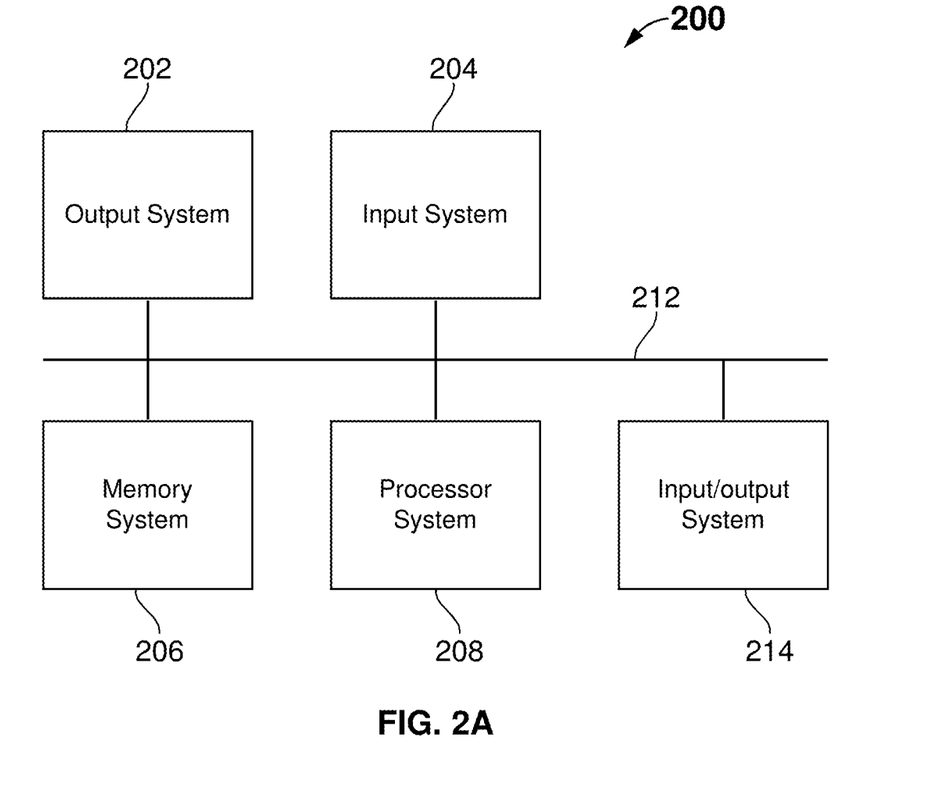
FIG. 2A illustrates in a block diagram, an automated parsing pipeline system for anatomical localization and condition classification according to yet another embodiment.
Figure 2B:
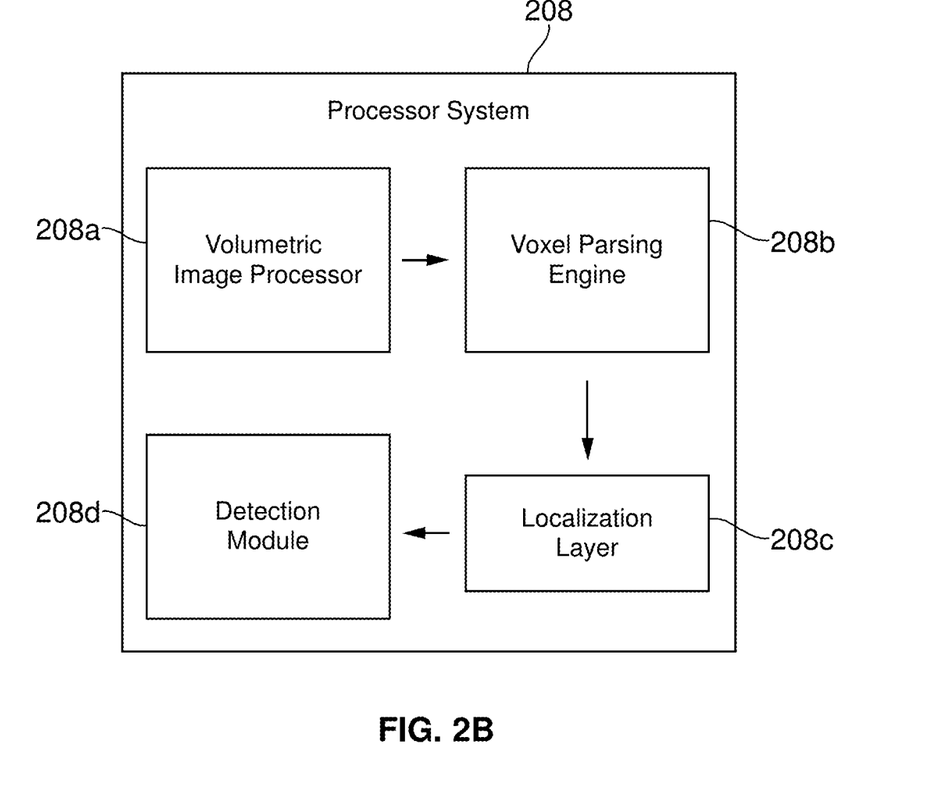
FIG. 2B illustrates in a block diagram, a processor system according to an embodiment.

FIG. 2A illustrates in a block diagram 200, an automated parsing pipeline system for anatomical localization and condition classification according to yet another embodiment. In an embodiment, the system comprises an input system 204, an output system 202, a memory system or unit 206, a processor system 208, an input/output system 214 and an interface 212. Referring to FIG. 2B, the processor system 208 comprises a volumetric image processor 208a, a voxel parsing engine 208b in communication with the volumetric image processor 208a, a localization layer 208e in communication with the voxel parsing engine 208 and a detection module 208d in communication with the localization module 208c. The processor 208 is configured to receive at least one volumetric image via an input system 202. At least one received volumetric image comprise a 3-D pixel array. The 3-D pixel array is pre-processed to convert into an array of Hounsfield Unit (HU) radio intensity measurements. Then, the processor 208 is configured to parse the received volumetric image data into at least a single image frame field of view by the said volumetric image processor 208a.

The anatomical structures residing in the at least single field of view is localized by assigning each voxel a distinct anatomical structure by the voxel parsing engine 208b.

The processor 208 is configured to select all voxels belonging to the localized anatomical structure by finding a minimal bounding rectangle around the voxels and the surrounding region for cropping as a defined anatomical structure by the localization layer 208c. Then, the conditions for each defined anatomical structure within the cropped image is classified by a detection module or classification layer 208d.

Below is an example of a hypothetical use case where the _colors of the _Image needs to be inverted, retaining the same transparency as the original image frame, for further analysis. The resulting pixel matrix is broken down to its individual pixel, tagged, and assigned an identity in the pixel matrix layer, before being passed onto the pixel aggregator for mapping into the pixel identity database (not shown). The following represents an illustrative algorithm:

Step 1: Load the _Image into memory
Step 2: Retrieve a _pixel from the pixel matrix
Step 3: Retrieve the _color of the _pixel computed in Step 2
Step 4: invert the _color of the _pixel from Step 3 into inverse for each component R, G &B
Step 5: Store the _color computed in Step 4 back to the pixel matrix
Step 6: Repeat Steps 2-5, for all pixels.
Step 7: Update the _Image with the newly computed pixel matrix.

The following represents illustrative pseudo code:

```
_Image image;
_pixels = image. GetPixelMatrix ( );
for ( int h = 0; h < image.height; h++ )
{
    for ( int w = 0; w < image.width; w++ )
    {
        _color color = pixels [h] [w];
        color = _color ( 255 - color.R, 255 - color.G,
        255 - color.B, color.A );
        _ pixels [h] [w] = color;
    }
}
image.SetPixelMatrix ( _pixels );
```

The following example demonstrates a possible hashing of the pixel identities. It uses the color names as keys for each bucket.

Hash map<String, _Color, Int, Int>pixel Identity=new Hash map<String, _Color, Int, Int>( );
pixelIdentity.insert ("red", _Color (255, 0, 0, 255), 0, 0);
pixelIdentity.insert ("red", _Color (224, 0, 0, 255), 0, 1);
pixelIdentity.insert ("blue", _Color (0, 0, 255, 255), 350, 0);
pixelIdentity.insert ("blue", _Color (0, 0, 230, 255), 350, 1);

The above pseudo code snippet demonstrates the possibility of grouping similar Alternatively, the data can be flattened and encoded into one value for hashing.

Figure 3A:
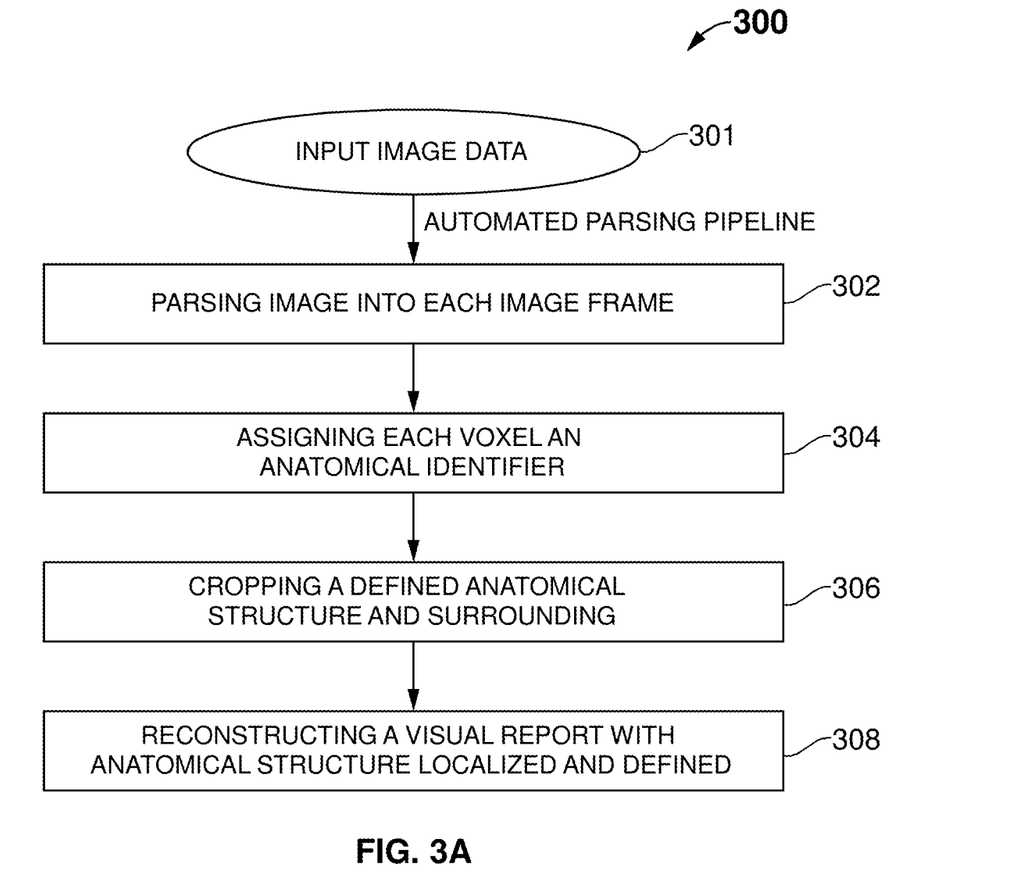
FIG. 3A. illustrates in a flow diagram, an automated parsing pipeline method for anatomical localization and condition classification, according to an embodiment.

For example: Hash map<String, _Color, Int, Int>pixel Identity=new Hash map<String, _Color, Int, Int>( );
pixelIdentity.insert ("red", _Color (255, 0, 0, 255), 0, 0);
can be written as: Hash map<String, String>pixelIdentity=new Hash map<String, String>( )
pixelIdentity.insert ("red", "2550000002550000000000000000000000");

FIG. 3A illustrates in a flow diagram 300, an automated parsing pipeline method for anatomical localization and condition classification, according to an embodiment. At step 301, an input image data is received. In one embodiment, the image data is a volumetric image data. At step 302, the received volumetric image is parsed into at least a single image frame field of view. The parsed volumetric image is pre-processed by controlling image intensity value.

At step 304, a tooth or anatomical structure inside the pre-processed and parsed volumetric image is localized and identified by tooth number. At step 306, the identified tooth and surrounding context within the localized volumetric image are extracted. At step 308, a visual report is reconstructed with localized and defined anatomical structure. In some embodiments, the visual reports include, but not limited to, an endodontic report (with focus on tooth's root/canal system and its treatment state), an implantation report (with focus on the area where the tooth is missing), and a dystopic tooth report for tooth extraction (with focus on the area of dystopic/impacted teeth).

Figure 3B:
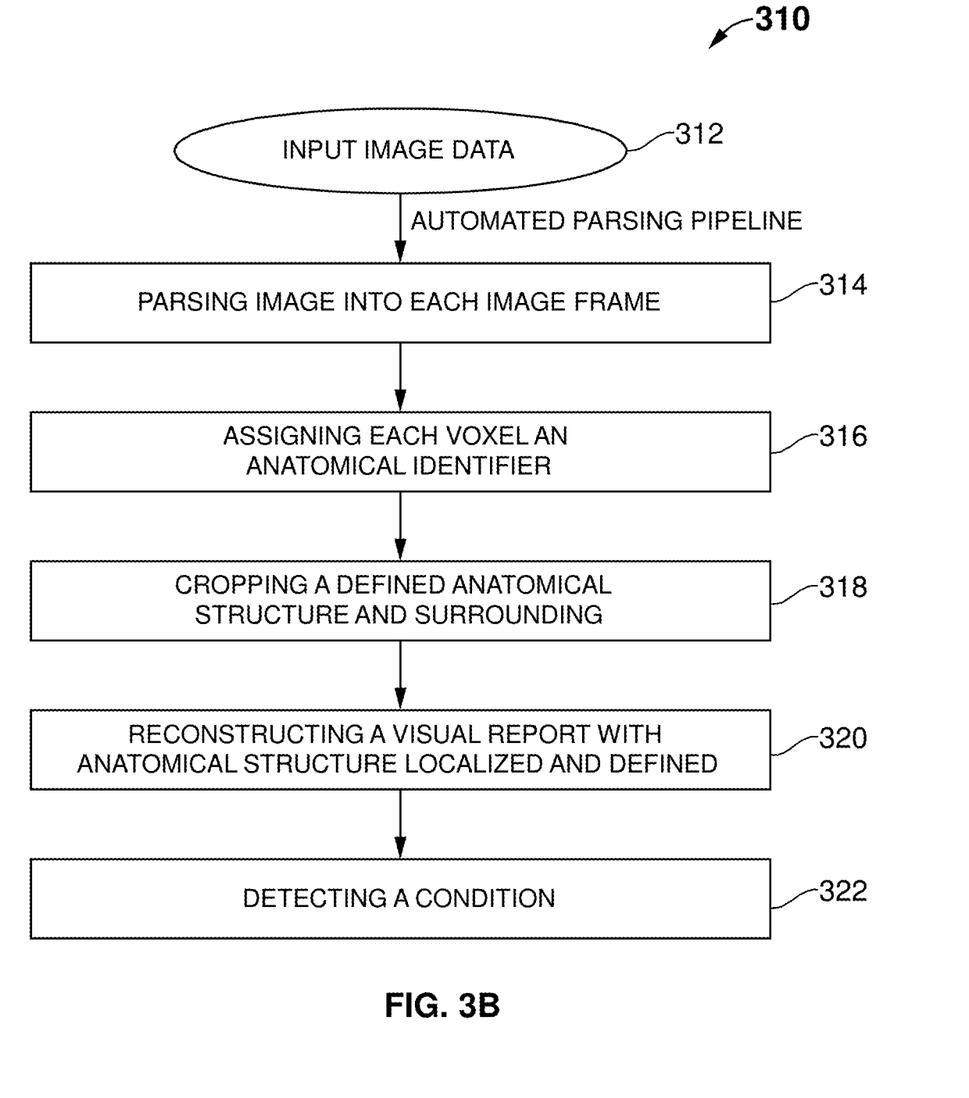
FIG. 3B illustrates in a flow diagram, an automated parsing pipeline method for anatomical localization and condition classification, according to another embodiment.

FIG. 3B illustrates in a flow diagram 310, an automated parsing pipeline method for anatomical localization and condition classification, according to another embodiment. At step 312, at least one volumetric image data is received from a radio-image gathering source by a volumetric image processor. At step 314, the received volumetric image data is parsed into at least a single image frame field of view by the volumetric image processor. At least single image frame field of view is pre-processed by controlling image intensity value by the volumetric image processor. At step 316, an anatomical structure residing in the at least single pre-processed field of view is localized by assigning each voxel a distinct anatomical structure ID by the voxel parsing engine. At step 318, all voxels belonging to the localized anatomical structure is selected by finding a minimal bounding rectangle around the voxels and the surrounding region for cropping as a defined anatomical structure by the localization layer. At step 320, a visual report is reconstructed with defined and localized anatomical structure. At step 322, conditions for each defined anatomical structure is classified within the cropped image by the classification layer.

Figure 4:
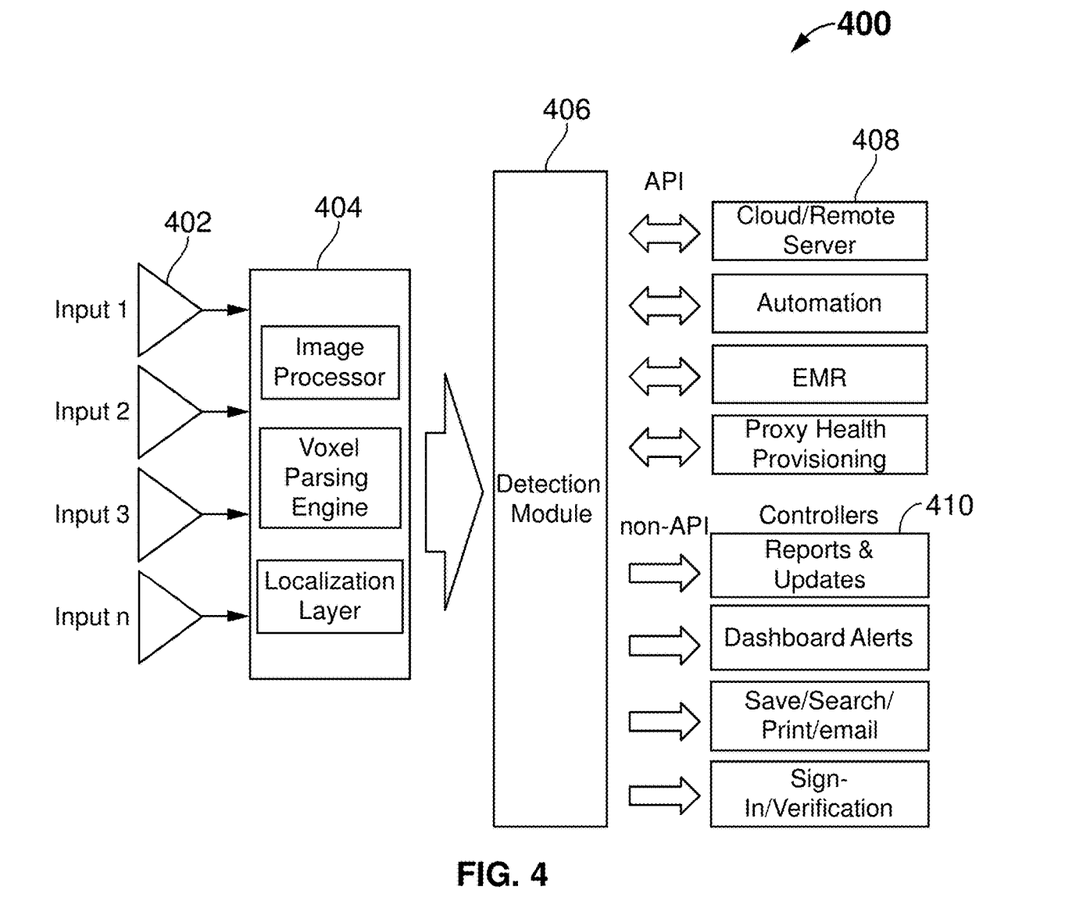
FIG. 4 illustrates in a block diagram, the automated parsing pipeline architecture according to an embodiment.

FIG. 4 illustrates in a block diagram 400, the automated parsing pipeline architecture according to an embodiment. According to an embodiment, the system is configured to receive input image data from a plurality of capturing devices, or input event sources 402. A processor 404 including an image processor, a voxel parsing engine and a localization layer. The image processor is configured to parse image into each image frame and preprocess the parsed image. The voxel parsing engine is configured to configured to localize an anatomical structure residing in the at least single pre-processed field of view by assigning each voxel a distinct anatomical structure ID. The localization layer is configured to select all voxels belonging to the localized anatomical structure by finding a minimal bounding rectangle around the voxels and the surrounding region for cropping as a defined anatomical structure. The detection module 406 is configured to detect the condition of the defined anatomical structure. The detected condition could be sent to the cloud/remote server, for automation, to EMR and to proxy health provisioning 408. In another embodiment, detected condition could be sent to controllers 410. The controllers 410 includes reports and updates, dashboard alerts, export option or store option to save, search, print or email and sign-in/verification unit.

Figure 5:
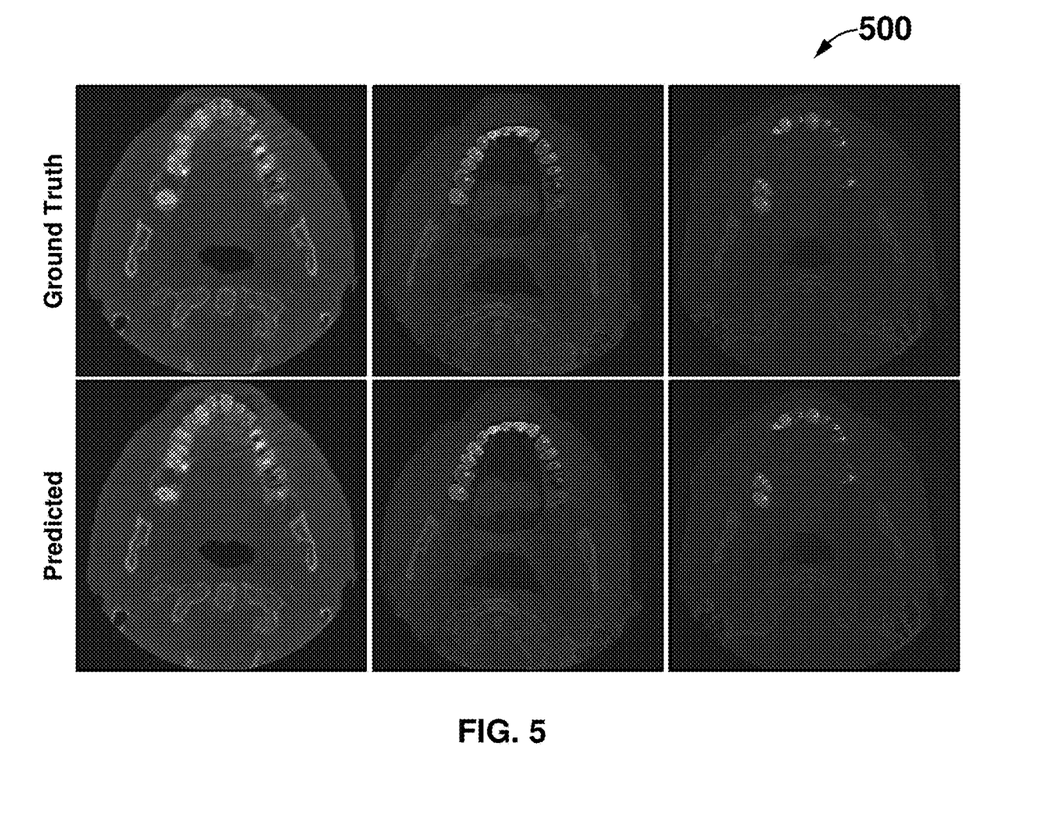
FIG. 5 illustrates in a screenshot, an example of ground truth and predicted masks in an embodiment of the present invention.

Referring to FIG. 5, an example screenshot 500 of tooth localization done by the present system, is illustrated. This figure shows examples of teeth segmentation at axial slices of 3D tensor.

Problem: Formulating the problem of tooth localization as a 33-class semantic segmentation, Therefore, each of the 32 teeth and the background are interpreted as separate classes.

Model: A V-Net-based fully convolutional network is used. V-Net is a 6-level deep, with widths of 32; 64; 128, 256; 512; and 1024. The final layer has an output width of 33, interpreted as a softmax distribution over each voxel, assigning it to either the background or one of 32 teeth. Each block contains 3*3*3 convolutions with padding of 1 and stride of 1, followed by ReLU non-linear activations and a dropout with 0:1 rate. Instance normalization before each convolution is used. Batch normalization was not suitable in this case, as long as there is only one example in batch (GPU memory limits); therefore, batch statistics are not determined.

Different architecture modifications were tried during the research stage. For example, an architecture with 64; 64; 128; 128; 256; 256 units per layer leads to the vanishing gradient flow and, thus, no training. On the other hand, reducing architecture layers to the first three (three down and three up) gives a comparable result to the proposed model, though the final loss remains higher.

Loss function: Let R be the ground truth segmentation with voxel values ri (0 or 1 for each class), and P the predicted probabilistic map for each class with voxel values pi. As a loss function we use soft negative multi-class Jaccard similarity, that can be defined as:

$$\text{Jaccard Multi class Loss} = 1 - \frac{1}{N}\sum_{i=0}^{N}\frac{p_i r_i + \epsilon}{p_i + r_i - p_i r_i + \epsilon'}$$

where N is the number of classes, which in our case is 32, and ε is a loss function stability coefficient that helps to avoid a numerical issue of dividing by zero. Then the model is trained to convergence using an Adam optimizer with learning rate of 1e-4 and weight decay 1e-8. A batch size of 1 is used due to the large memory requirements of using volumetric data and models. The training is stopped after 200 epochs and the latest checkpoint is used (validation loss does not increase after reaching the convergence plateau).

Results: The localization model is able to achieve a loss value of 0:28 on a test set. The background class loss is 0:0027, which means the model is a capable 2-way "tooth/ not a tooth" segmentor. The localization intersection over union (IoU) between the tooth's ground truth volumetric bounding box and the model-predicted bounding box is also defined. In the case where a tooth is missing from ground truth and the model predicted any positive voxels (i.e. the ground truth bounding box is not defined), localization IoU is set to 0. In the case where a tooth is missing from ground truth and the model did not predict any positive voxels for it, localization IoU is set to 1. For a human-interpretable metric, tooth localization accuracy which is a percent of teeth is used that have a localization IoU greater than 0:3 by definition. The relatively low threshold value of 0:3 was decided from the manual observation that even low localization IoU values are enough to approximately localize teeth for the downstream processing. The localization model achieved a value of 0:963 IoU metric on the test set, which, on average, equates to the incorrect localization of 1 of 32 teeth.

Figure 6A:
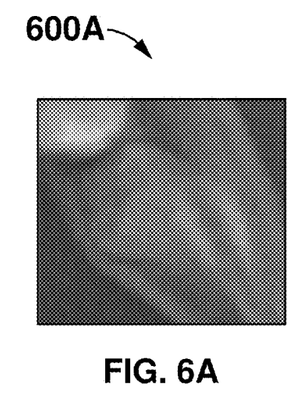
FIGS. 6A, 6B & 6C illustrates in a screenshot, the extraction of anatomical structure by the localization model of the system in an embodiment of the present invention.
Figure 6B:
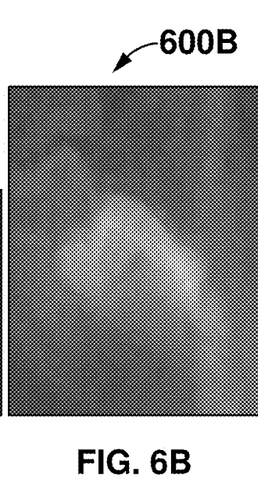
Figure 6C:
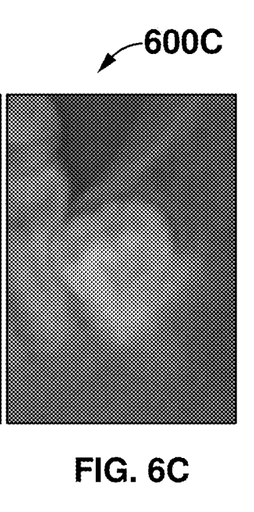

Referring to FIGS. 6A-6C, an example screenshot (600A, 600B, 600B) of tooth sub-volume extraction done by the present system, illustrated.

In order to focus the downstream classification model on describing a specific tooth of interest, the tooth and its surroundings is extracted from the original study as a rectangular volumetric region, centered on the tooth. In order to get the coordinates of the tooth, the upstream segmentation mask is used. The predicted volumetric binary mask of each tooth is preprocessed by applying erosion, dilation, and then selecting the largest connected component. A minimum bounding rectangle is found around the predicted volumetric mask. Then, the bounding box is extended by 15 mm vertically and 8 mm horizontally (equally in all directions) to capture the tooth context and to correct possibly weak localizer performance. Finally, a corresponding sub-volume is extracted from the original clipped image, rescale it to 643 and pass it on to the classifier. An example of a sub-volume bounding box is presented in FIGS. 6A-6C.

Figure 7:
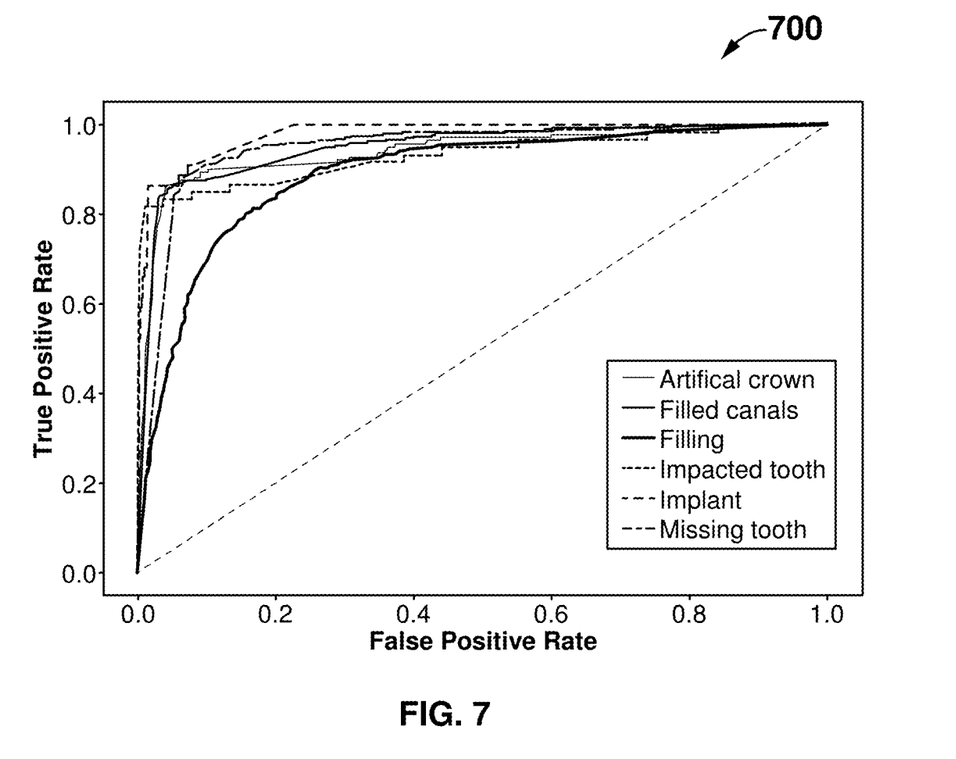
FIG. 7 illustrates in a graph, receiver operating characteristic (ROC) curve of a predicted tooth condition in an embodiment of the present invention.

Referring to FIG. 7, a receiver operating characteristic (ROC) curve 700 of a predicted tooth condition is illustrated.

Model: The classification model has a DenseNet architecture. The only difference between the original and implementation of DenseNet by the present invention is a replacement of the 2D convolution layers with 3D ones. 4 dense blocks of 6 layers is used, with a growth rate of 48, and a compression factor of 0:5. After passing the 643 input through 4 dense blocks followed by down-sampling transitions, the resulting feature map is 548×2×2×2. This feature map is flattened and passed through a final linear layer that outputs 6 logits—each for a type of abnormality.

Loss function: Since tooth conditions are not mutually exclusive, binary cross entropy is used as a loss. To handle class imbalance, weight each condition loss inversely proportional to its frequency (positive rate) in the training set. Suppose that Fi is the frequency of condition i, pi is its predicted probability (sigmoid on output of network) and ti is ground truth. Then: Li=(1−Fi)·Ti·log pi+Fi·(1−ti)·log(1−pi) is the loss function for condition i. The final example loss is taken as an average of the 6 condition losses.

| | Artificial crowns | Filling canals | Filling | Impacted tooth | Implant | Missing |
|---|---|---|---|---|---|---|
| ROC AUC | 0.941 | 0.95 | 0.892 | 0.931 | 0.979 | 0.946 |
| Condition frequency | 0.092 | 0.129 | 0.215 | 0.018 | 0.015 | 0.145 |

Results: The classification model achieved average area under the receiver operating characteristic curve (ROC AUC) of 0:94 across the 6 conditions. Per-condition scores are presented in above table. Receiver operating characteristic (ROC) curves 700 of the 6 predicted conditions are illustrated in FIG. 7.

Advantageously, the present invention provides an end-to-end pipeline for detecting state or condition of the teeth in dental 3D CBCT scans. The condition of the teeth is detected by localizing each present tooth inside an image volume and predicting condition of the tooth from the volumetric image of a tooth and its surroundings. Further, the performance of the localization model allows to build a high-quality 2D panoramic reconstruction, which provides a familiar and convenient way for a dentist to inspect a 3D CBCT image. The performance of the pipeline is improved by adding volumetric data augmentations during training; reformulating the localization task as instance segmentation instead of semantic segmentation; reformulating the localization task as object detection, and use of different class imbalance handling approaches for the classification model. Alternatively, the jaw region of interest is localized and extracted as a first step in the pipeline. The jaw region typically takes around 30% of the image volume and has adequate visual distinction. Extracting it with a shallow/ small model would allow for larger downstream models. Further, the diagnostic coverage of the present invention extends from basic tooth conditions to other diagnostically relevant conditions and pathologies.

The figures illustrate the architecture, functionality, and operation of possible implementations of systems, methods and computer program products according to various embodiments of the present invention. It should also be noted that, in some alternative implementations, the functions noted/illustrated may occur out of the order noted. For example, two blocks shown in succession may, in fact, be executed substantially concurrently, or the blocks may sometimes be executed in the reverse order, depending upon the functionality involved.

Since various possible embodiments might be made of the above invention, and since various changes might be made in the embodiments above set forth, it is to be understood that all matter herein described or shown in the accompanying drawings is to be interpreted as illustrative and not to be considered in a limiting sense. Thus, it will be understood by those skilled in the art of creating independent multi-layered virtual workspace applications designed for use with independent multiple input systems that although the preferred and alternate embodiments have been shown and described in accordance with the Patent Statutes, the invention is not limited thereto or thereby.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Some portions of embodiments disclosed are implemented as a program product for use with an embedded processor. The program(s) of the program product defines functions of the embodiments (including the methods described herein) and can be contained on a variety of signal-bearing media. Illustrative signal-bearing media include, but are not limited to: (i) information permanently stored on non-writable storage media (e.g., read-only memory devices within a computer such as CD-ROM disks readable by a CD-ROM drive); (ii) alterable information stored on writable storage media (e.g., floppy disks within a diskette drive or hard-disk drive, solid state disk drive, etc.); and (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-accessible format and hence executable instructions. Also, programs are comprised of variables and data structures that either reside locally to the program or are found in memory or on storage devices. In addition, various programs described may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

The present invention and some of its advantages have been described in detail for some embodiments. It should be understood that although the system and process is described with reference to Pixel Matrix Data Systems and Methods, the system and process may be used in other contexts as well. It should also be understood that various changes, substitutions and alterations can be made herein without departing from the spirit and scope of the invention as defined by the appended claims. An embodiment of the invention may achieve multiple objectives, but not every embodiment falling within the scope of the attached claims will achieve every objective. Moreover, the scope of the present application is not intended to be limited to the particular embodiments of the process, machine, manufacture, and composition of matter, means, methods and steps described in the specification. A person having ordinary skill in the art will readily appreciate from the disclosure of the present invention that processes, machines, manufacture, compositions of matter, means, methods, or steps, presently existing or later to be developed are equivalent to, and fall within the scope of, what is claimed. Accordingly, the appended claims are intended to include within their scope such processes, machines, manufacture, compositions of matter, means, methods, or steps.

We claim:

1. An automated parsing pipeline system for anatomical localization and condition classification, said system comprising:
    a processor;
    a non-transitory storage element coupled to the processor;
    encoded instructions stored in the nor-transitory storage element, wherein the encoded instructions when implemented by the processor, configure the automated parsing pipeline system to:
        receive at least one volumetric image;
        parse the received volumetric image into at least a single image frame field of view;
        localize a present tooth inside the parsed volumetric image and identifying it by number;
        extract the identified tooth and surrounding context within the localized volumetric image; and
        classify a tooth's conditions based on the extracted volumetric image using at least one of a multi-task approach, one network per condition approach, or a sub-network approach, wherein the multi-task approach is a single network outputting a prediction for multiple tooth conditions, the one network per condition approach is a single network outputting a prediction for a single tooth condition, and the sub-network approach is multiple networks outputting predictions for multiple tooth conditions.

2. The system of claim 1, wherein the at least one received volumetric image comprises a 3-D pixel array.

3. The system of claim 2, further configured to pre-process by converting the 3-D pixel array into an array of Hounsfield Unit (HU) radio intensity measurements.

4. The system of claim 1, further configured to pre-process at least one of the localization or classification steps by rescaling using linear interpolation.

5. The system of claim 1, wherein the pre-processing comprises using any one of a normalization schemes to account for variations in image value intensity depending on at least one of an input or output of volumetric image.

6. The system of claim 1, wherein the localization is achieved using a V-Net-based fully convolutional neural network.

7. The system of claim 1, further configured to extract anatomical structure by finding a minimum bounding rectangle around the localized and identified tooth.

8. The system of claim 7, wherein the bounding rectangle extends by at least 15 mm vertically and 8 mm horizontally (equally in all directions) to capture the tooth and surrounding context.

9. The system of claim 1, wherein the classification is achieved using a DenseNet 3-D convolutional neural network.

10. A method for localizing a tooth and classifying a tooth condition, said method comprising the steps of:
    receiving at least one volumetric image;
    parsing the received volumetric image into at least a single image frame field of view;
    localizing a present tooth inside the parsed volumetric image and identifying it by number;
    extracting the identified tooth and surrounding context within the localized volumetric image; and
    classify a tooth's conditions based on the extracted volumetric image using at least one of a multi-task approach, one network per condition approach, or a sub-network approach, wherein the multi-task approach is a single network outputting a prediction for multiple tooth conditions, the one network per condition approach is a single network outputting a prediction for a single tooth condition, and the sub-network approach is multiple networks outputting predictions for multiple tooth conditions.

11. The method of claim 10, wherein the at least one received volumetric image comprises a 3-D pixel array.

12. The method of claim 10, further includes a step of: pre-processing by converting the 3-D pixel array into an array of Hounsfield Unit (HU) radio intensity measurements.

13. The method of claim 10, wherein the pre-processing for at least one of the localization or classification steps comprises rescaling using linear interpolation.

14. The method of claim 10, wherein the pre-processing comprises using any one of a normalization schemes to account for variations in image value intensity depending on at least one of an input or output of volumetric image.

15. The method of claim 10, wherein the localization is achieved using a V-Net-based fully convolutional neural network.

16. The method of claim 10, further comprises a step of: achieving extraction by finding a minimum bounding rectangle around the localized and identified tooth.

17. The method of claim 16, wherein the bounding rectangle extends by at least 15 mm vertically and 8 mm horizontally (equally in all directions) to capture the tooth and surrounding context.

18. The method of claim 10, wherein the classification is achieved using a DenseNet 3-D convolutional neural network.

* * * * *